United States Patent
Dobbin

(10) Patent No.: US 6,772,896 B1
(45) Date of Patent: Aug. 10, 2004

(54) EMERGENCY CASE

(76) Inventor: Kevin Dobbin, 5936 Brandon La., Port Orange, FL (US) 32127

( * ) Notice: Subject to any disclaimer, the term of this patent is extended or adjusted under 35 U.S.C. 154(b) by 0 days.

(21) Appl. No.: 10/101,414

(22) Filed: Mar. 20, 2002

Related U.S. Application Data

(63) Continuation-in-part of application No. 09/774,808, filed on Feb. 1, 2001, now abandoned.

(51) Int. Cl.[7] .............................................. B65D 21/032
(52) U.S. Cl. ...................................................... 220/4.27
(58) Field of Search ................................ 220/4.27, 522, 220/528, 526, 4.26, 819, 849, 23.4; 206/523, 564, 590, 592, 508

(56) References Cited

U.S. PATENT DOCUMENTS

| | | | | |
|---|---|---|---|---|
| 2,836,288 A | * | 5/1958 | Atchison | 206/89 |
| 2,840,256 A | * | 6/1958 | Cobb, Jr. | 220/4.26 |
| 4,998,616 A | * | 3/1991 | Hillinger | 206/748 |
| 5,344,024 A | * | 9/1994 | Cohu | 206/526 |
| 5,515,974 A | * | 5/1996 | Higson | 206/570 |
| 6,010,670 A | * | 1/2000 | Berry, Jr. | 422/295 |
| 6,032,421 A | * | 3/2000 | Yamada | 52/79.8 |

* cited by examiner

*Primary Examiner*—Stephen Castellano
(74) *Attorney, Agent, or Firm*—Patent & Trademark Services; Joseph H. McGlynn

(57) ABSTRACT

A case for carrying items that will be useful in an emergency. The case has multiple layers which are hinged together with a watertight seal between layers. Each layer is made up of multiple compartments and the walls between the compartments have a tongue and groove joint with a seal therebetween.

11 Claims, 1 Drawing Sheet

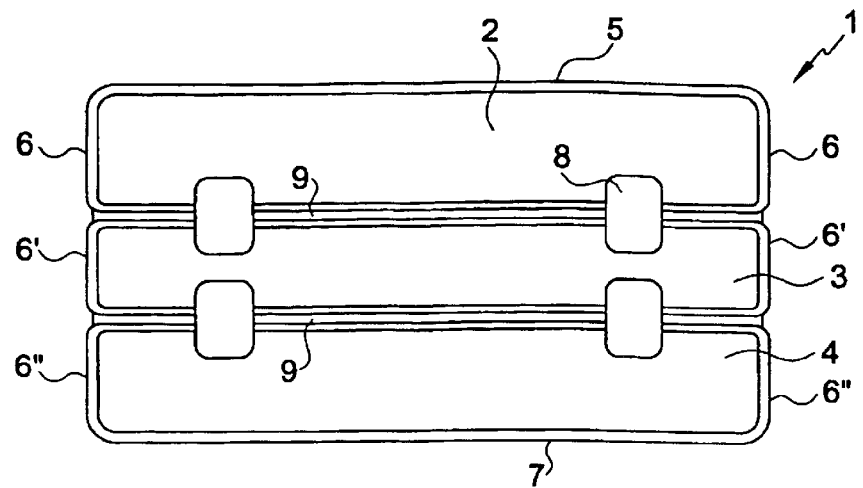
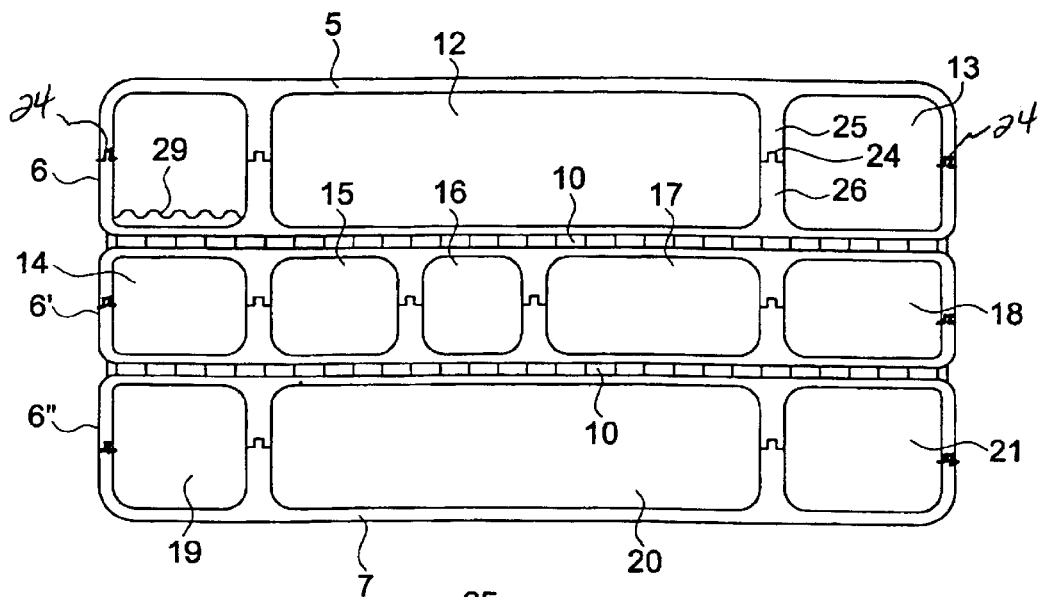
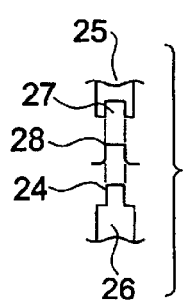

EMERGENCY CASE

This is a Continuation in Part of Ser. No. 09/774,808, filed Feb. 1, 2001, now abandoned.

BACKGROUND OF THE INVENTION

This invention relates, in general, to cases, and, in particular, to cases which carry items needed to respond to emergencies.

DESCRIPTION OF THE PRIOR ART

In the prior art various types of cases have been proposed. For example, U.S. Patent No. to Carpenter discloses an emergency case having compartments for items such as a flashlight, blanket, etc.

The patent to Higson discloses an emergency case having compartments for items such as a flashlight, blanket, etc and a lid with a compartment for items such as instructions.

The patent to Bugyi discloses an emergency case having a hinged lid which forms a tray when opened.

The patent to Toulmin, Jr. discloses an apparatus fro air borne communication and shelter equipment.

SUMMARY OF THE INVENTION

The present invention is directed to a case for carrying items that will be useful in an emergency. The case has multiple layers which are hinged together with a watertight seal between layers. Each layer is made up of multiple compartments and the walls between the compartments have a tongue and groove joint with a seal therebetween.

It is an object of the present invention to provide a new and improved emergency case.

It is an object of the present invention to provide a new and improved emergency case which is completely sealed to protect the contents.

It is an object of the present invention to provide a new and improved emergency case which has interlocking vertical walls to allow different configurations of compartments to be used.

These and other objects and advantages of the present invention will be fully apparent from the following description, when taken in connection with the annexed drawings.

BRIEF DESCRIPTION OF THE DRAWINGS

FIG. 1 is front view of the exterior of the present invention.

FIG. 2 is an internal view of the present invention with the back wall removed to show the interior compartments.

FIG. 3 is a partial view of one of the vertical walls of the present invention.

DESCRIPTION OF THE PREFERRED EMBODIMENT

Referring now to the drawings in greater detail, FIG. 1 shows an emergency case 1 in which a user can store various items such as, but not limited to, blankets, raincoat or poncho, toiletries, candles, glasses, batteries, flashlight, matches, important documents, cellular telephone and other essential items which would be useful in the case of an emergency. By storing these types of items in the case at all times, the user would always have necessary items in one convenient place in the case of an emergency.

As shown in FIG. 1, the case has three layers 2, 3 and 4. It should be understood that the three layers are merely for illustrational purposes and less than or more than three layers could be used without departing from the scope of the invention. The case 1 has a top surface 5 and a bottom surface 7 and side surfaces or walls 6, 6', 6". In addition, a seal such as a rubber )-ring 9 is placed between the layers to prevent water or other debris from entering the case. Also, each layer has at least one pull tight latch 8 which will secure the layers 2, 3, 4 together and which will compress the seal 9 when they are fastened. The latches 8 are conventional latches, therefore, no further description is necessary or will be given.

As shown in FIG. 2, which is a back view of the case with the rear wall removed to show the internal compartments, the layers are divided into compartments 11, 12, 13, 14, 15, 16, 17, 18, 19, 20, and 21. The number of compartments, the shape of the compartments and their location with respect to each other are merely for illustrational purposes. The number, shape and location can be changed without departing from the scope of the invention. The layers 2, 3, 4 are hinged together with a continuous piano hinge 10. The hinge should be made from a non-corrosive material such as, but not limited to, stainless steel. Each compartment 11, 12, 13, 14, 15, 16, 17, 18, 19, 20, and 21 could be fitted with a soft foam material 29 to protect the items stored in the compartments if necessary. Also, it should be noted that only one compartment 11 is shown having the foam 29, however, each compartment could be provided with the foam 29 or some compartments could be provided with the foam and other compartments could be unlined. Which compartments are lined and which are not lined would depend on the type of items stored therein, and whether the items need protection or not. Also, the lining could be made removable so the user could decide which compartments need the lining, or the lining could be a permanent part of each compartment, without departing from the scope of the invention.

As shown in FIG. 3, each vertical wall is made in parts 25, 26 which are secured together by one part 25 having a groove 27 which receives a tab or tongue 24 on the other part 26 of the wall. In addition, a seal 28 is placed in between the parts 25, 26. The seal is shaped on one end to fit into the groove 27 and the other end of the seal 28 is shape to receive the tab or tongue 24. In this manner a seal is maintained between the various compartments to provide water tight integrity. Therefore, even if one compartment leaked, the seals to adjacent compartments would prevent the water from leaking from one compartment to another compartment.

Although the Emergency Case and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A case for storing emergency items, said case comprising:

at least two layers which are hinged together to form a closed container, a seal interposed between said at least two layers to seal an interior of the case, means for securing said at least two layers together and for allowing said at least two layers to be opened, each layer being formed of a plurality of compartments, each of said plurality of compartments having vertical walls forming said plurality of compartments, each of said vertical walls being formed of two parts which fit together to form a single wall.

2. The case for storing emergency items as claimed in claim 1, wherein said seal is an O-ring.

3. The case for storing emergency items as claimed in claim 2, wherein said O-ring is positioned around a circumference of said at least two layers.

4. The case for storing emergency items as claimed in claim 1, wherein said case comprises three layers.

5. The case for storing emergency items as claimed in claim 1, wherein at least some of said compartments is provided with a soft lining.

6. The case for storing emergency items as claimed in claim 1, wherein each of said vertical walls fit together by having one of said two parts formed of a shape that will engage a complementary shape on another of said two parts.

7. The case for storing emergency items as claimed in claim 6, wherein said shape on one of said two parts is a groove, and the shape on said another of said two parts is a tongue.

8. The case for storing emergency items as claimed in claim 6, wherein a seal is positioned between said one of said two parts and said another of said two parts.

9. The case for storing emergency items as claimed in claim 8, wherein said seal has a first part which fits into one of said two parts and which receives another of said two parts.

10. A case for storing emergency items, said case comprising:

at least two layers which are hinged together to form a dosed container, a seal interposed between said at least two layers to seal an interior of the case, means for securing said at least two layers together and for allowing said at least two layers to be opened, each layer being formed of a plurality of compartments, each of said plurality of compartments having vertical walls forming said plurality of compartments, each of said vertical walls being formed of two parts which fit together to form a single wall, each of said vertical walls being divided in a vertical direction and have means extending in said vertical direction to secure each of said vertical walls together.

11. The case for storing emergency items as claimed in claim 10, wherein said means extending in said vertical direction to secure each of said vertical walls together is a groove on one of said vertical walls and a tongue on another of said vertical walls.

\* \* \* \* \*